United States Patent [19]

Limousin

[11] Patent Number: 5,514,161
[45] Date of Patent: May 7, 1996

[54] METHODS AND APPARATUS FOR CONTROLLING ATRIAL STIMULATION IN A DOUBLE ATRIAL TRIPLE CHAMBER CARDIAC PACEMAKER

[75] Inventor: Marcel Limousin, Montrouge, France

[73] Assignee: ELA Medical S.A., Montrouge, France

[21] Appl. No.: 416,308

[22] Filed: Apr. 4, 1995

[30] Foreign Application Priority Data

Apr. 5, 1994 [FR] France .................... 94 03988

[51] Int. Cl.$^6$ .................... A61N 1/368
[52] U.S. Cl. .................... 607/9; 607/14
[58] Field of Search .................... 607/9, 14, 19

[56] References Cited

U.S. PATENT DOCUMENTS

| | | |
|---|---|---|
| 4,932,406 | 6/1990 | Berkovits . |
| 5,107,850 | 4/1992 | Olive . |
| 5,226,415 | 7/1993 | Girodo et al. . |

FOREIGN PATENT DOCUMENTS

| | | | |
|---|---|---|---|
| 2544989 | 4/1983 | France .................... | A61N 1/36 |
| WO9209331 | 6/1992 | WIPO .................... | A61N 1/368 |
| WO9214511 | 9/1992 | WIPO .................... | A61N 1/368 |

Primary Examiner—William E. Kamm
Assistant Examiner—Scott M. Getzow
Attorney, Agent, or Firm—Orrick Herrington & Sutcliffe

[57] ABSTRACT

Process for controlling a double atrial triple chamber pacemaker having a right atrial electrode and a left atrial electrode connected to one and the same atrial circuit for the detection/stimulation of the atrium, as well as a ventricular electrode connected to a ventricular circuit for the detection/stimulation of the ventricle. The control process includes receiving at the input of the atrial circuit and the ventricular circuit a succession of depolarization signals, determining a possibly premature character of the depolarization signal sensed at the input of the atrial circuit, in case of determined prematurity, examining, during the duration of a predetermined window of listening, signals sensed at the input of the ventricular circuit and, in case of a ventricular signal reception, inhibiting all correlated atrial stimulation, and in the absence of sensing a ventricular signal, proceeding to an atrial stimulation at both atria at the end of the listening window duration, and, in the case of no prematurity character being found, proceeding to an immediate atrial stimulation in both atria synchronous to the detection of the sensed atrial depolarization signal.

6 Claims, 1 Drawing Sheet

METHODS AND APPARATUS FOR CONTROLLING ATRIAL STIMULATION IN A DOUBLE ATRIAL TRIPLE CHAMBER CARDIAC PACEMAKER

FIELD OF THE INVENTION

The present invention concerns a cardiac pacemaker of the "double atrial triple chamber" type, in which there is possible sensing and stimulation of the right ventricle and each of the two atria, right and left.

BACKGROUND OF THE INVENTION

Triple chamber pacemakers typically include a ventricular electrode (generally a bipolar endocardial lead), and two atrial electrodes which are respectively implanted on each of the two atria and commonly connected to a corresponding single input port of the pacemaker. The common connection is typically a Y connector.

In a classic "bipolar electrode" the two conductive extremities, namely the distal and proximal terminals, are separated by only a few millimeters. In the atrial bipolar electrode for use in a double atrial triple chamber pacemaker in accordance with the present invention, however, the distal and proximal terminals are relatively spaced apart much further, e.g., a typical distance on the order of 5 cm, so that one electrode terminal is implanted in the right atrium and the other electrode terminal is implanted in the left atrium.

Triple chamber cardiac pacemakers have been used in a relatively satisfactory manner for some years. They are useful in connection with patients having indications presenting an "intra-atrial block" sinusal disorder, in which there is a deficient propagation of conduction (either insufficient or too long) from the right atrium to the left atrium.

Thus, if only one of the atria is stimulated (e.g., the right atrium, as in the classic situation of a "double chamber" pacemaker), the other atrium (e.g., the left atrium), which is not stimulated, would receive the depolarization wave coming from the stimulated atrium, if at all, after an excessively long period. In some cases, the period is longer than the atrial-ventricular delay (AV delay). Such a phenomenon can result in a contraction of ventricles occurring before the left atrium has finished draining, and, therefore, before the mistral valve has closed. This produces a counter-flow of blood from the ventricle to the left atrium and a diminution of the hemodynamic efficiency.

In addition, the electrical desynchronisation of the two atria favors the occurrence of tachyarrhythmia events.

Further, it has been recognized that the inter-atrial propagation delay period increases with the patient's effort. Therefore, the increase of the physiological activity of the patient apparently favors the risk of appearance of a such a syndrome.

The known triple chamber pacemakers operate by stimulating the left and right atria in a simultaneous manner. This is done to avoid the appearance or the persistence of the aforementioned phenomenon. Nevertheless, clinical studies have revealed the appearance of atrial tachyarrhythmia (AT) for some patients, notwithstanding such a systematic, simultaneous stimulation of the two atria. These AT, whose origin had not up until now been able to be identified, typically necessitated further treatment of patients by medication (for example, by administering a beta-blocking therapy). However, such medicinal treatments have a certain residual failure rate, such that a medicinal treatment is not always sufficient to prevent the appearance of recurrent AT in some patients. In addition, the treatment of the recurrent AT by medication is contraindicated absolutely in some patients.

OBJECTS AND SUMMARY OF THE INVENTION

It is, therefore, an object of the invention is to provide an improved control process for a double atrial triple chamber cardiac pacemaker which overcomes almost totally the recurrent AT having an unknown origin, which is associated with this type of device. It is another object to do so while avoiding the additional use of all medicinal treatments, and therefore the difficulties linked to contraindications and to secondary effects of the anti-arrhythmic agents that were heretofore believed necessary to use in supplement to the triple chamber pacemaker in certain patients.

The invention is essentially based on the inventors' discovery of a probable cause of the recurrent AT associated with the triple chamber pacemakers. More particularly, the inventors have recognized that, as will be explained in more detail below, recurrent AT are probably a "PMT" (Pacemaker-Mediated Tachyrhythmia) generated by an intervening confusion of the significance of the signals sensed at the level of atrial circuit. The confusion is caused by the appearance at the atrial circuit of sensed atrial signals in the form of a wave doublet indicative of an inter-atrium propagation time interval that is significant, and of the ventricular depolarization waveform from an ectopic event, notably if the ectopic event is situated near the left atrium. This confusion of sensed signals can result in starting an AV delay period which leads to a ventricular stimulation that is in turn susceptible to induce a recurring AT, i.e., a PMT.

An object of the invention is, therefore, to discriminate the sensed signals, namely to avoid the confusion at the atrial circuit between sensed signals that are ventricular in origin and atrial in origin, and thus to avoid the releasing of a reentrant tachycardia (PMT) which might lead to a persistent AT from a previously unknown origin associated with the triple chamber stimulation.

Broadly, the invention concerns the improved control of a cardiac pacemaker of the double atrial triple chamber type, comprising a right atrial electrode and a left atrial electrode that are connected to the same atrial circuit for the detection and stimulation for the atria of the pacemaker, as well as a ventricular electrode connected to a ventricular circuit for the detection and stimulation of the ventricle.

One aspect of the invention concerns a control process characterized by the steps of:

receiving i.e., sensing, at the inputs of the atrial circuit and the ventricular circuit a succession of depolarization signals;

determining whether or not the signal received at the input of the atrial circuit has a prematurity character;

in case of a determined prematurity, examining, during a listening window of a predetermined duration, signals received at the input of the ventricular detection circuit, in the case of a ventricular signal reception during the listening window, inhibiting all correlated atrial stimulation; and in case of the absence of a ventricular signal reception during the listening window, stimulating the atria (both) at the end of the duration of the listening window; and in the case of no determined prematurity, proceeding to an immediate atria stimulation synchronous to the detection of the atrial depolarization signal sensed.

In one embodiment, the process step of determining whether or not the sensed signal has a prematurity character includes measuring the interval of time separating two successive atrial signals, determining one of (i) the diminution, or (ii) the rate of diminution of this measured interval of time, and comparing the determined diminution or rate of diminution to a predetermined limit value, such that the prematurity condition is determined to exist when the limit value is exceeded.

In a second embodiment, the process step of determining the prematurity includes measuring the interval of time separating two successive signals, which may be either two successive atrial or two successive ventricular signals, counting, beginning with the last sensed ventricular event, a period corresponding to a predetermined fraction of the measured time interval, and analyzing signals received at the input of the atrial circuit during said period, wherein the prematurity condition is determined to exist when a signal is sensed at the atrial circuit during the period.

Another aspect of the invention concerns apparatus for controlling the pacemaker which includes logic circuits configured and operable to perform the aforementioned stimulation control process. Such apparatus logic circuits may be a microprocessor executing a software program stored in a memory device and signal conditioning (and digital conversion) circuits for sensing depolarization signals and processing the sensed signals in the manner described, or discrete logic circuits including latches, counters, flip-flops, comparators and gates configured for performing the same functions, albeit in a different way.

BRIEF DESCRIPTION OF THE DRAWINGS

Other characteristics and advantages of the invention will appear to a person of ordinary skill in the art in view of the following description of a preferred embodiment of the invention, made with reference to drawings annexed, in which.

DETAILED DESCRIPTION OF THE DRAWINGS

Figure 1:
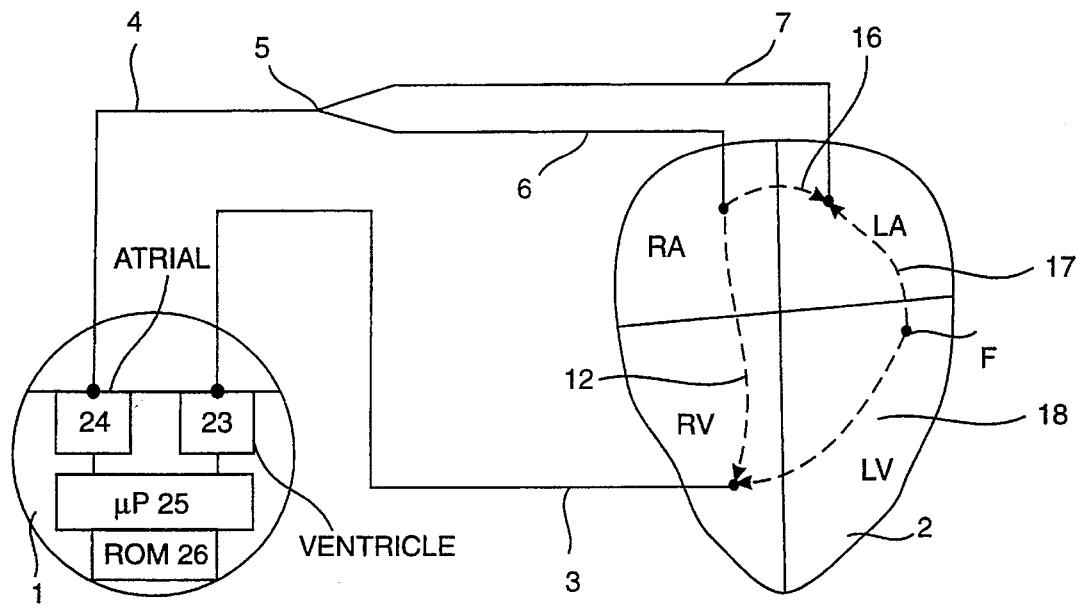
FIG. 1 is a schematic view of the connection of a double atrial triple chamber pacemaker and the implantation of the atrial and ventricular endocardial electrodes on the myocardia (muscle) of the different cardiac chambers.

With reference to FIG. 1, the reference 1 designates a cardiac pacemaker, that is a typical DDD or DDT type device. Pacemaker 1 is a double bipolar pacemaker, in which there is both atrial and ventricular signal detection and ventricular and atrial stimulation, functioning in triggered mode. A triggered mode refers to producing a stimulation from the sensing of a signal on the corresponding electrode or, in an imposed manner, in the absence of a sensed signal after a given predetermined time.

The pacemaker 1 is connected to the myocardia 2 by a configuration of the triple chamber type, that is to say with a ventricular electrode 3 connected to the right ventricle RV and a double atrial electrode 4 connected to each of the two atria, the right atrium RA and the left atrium LA, by the intermediary of a Y connector 5, and two respective electrode conductors (terminals) 6 and 7. As a result of Y connector 5, an atrial circuit 24 of detection/stimulation of the pacemaker 1 is connected to the electrode 4 at the common input, in a bipolar configuration for the detection and for delivering the stimulation pulse, and detects all signal received or sensed at each of electrodes 6 and 7 indifferently and, conversely, stimulates simultaneously and in an identical manner the two atria RA and LA. Such an atrial circuit 24 is well known in the art and may be of any type. The ventricular electrode 3 is connected to a ventricular circuit 23 for the sensing and stimulation of the ventricle, in a conventional manner well known in the art. Electrode 3 is preferably a conventional bipolar endocardial lead.

Such atrial circuits 24 and ventricular circuits 23 are known which can be separately and independently configured to sense cardiac activity in a bipolar mode or in a monopolar (unipolar) mode, the latter referencing one of the two bipolar terminals to the pacemaker case (relative ground). Suitable triple chamber cardiac pacemakers can be obtained by a modification of double chamber pacemakers such as those sold under the model name CHORUS II and CHORUS RM, available from ELA Medical of Montrouge France, and such that a double atrial electrode comprises two unipolar electrodes for implantation of one distal terminal in the left atrium and the other distal terminal in the right atrium and the Y connector. These CHORUS model pacemakers, similar to other double chamber pacemakers, include a microprocessor (25, FIG. 1) and ROM 26 containing software instructions suitable for executing a DDT mode (and perhaps other modes) of pacing and the signal discrimination as described herein. The construction and programming of a software routine, and fixing of the program in a ROM 26 (or other memory device), to implement the triple chamber operation of the present invention are believed to be within the ordinary skill of the art.

The signal sensed by atrial circuit 24 follows generally the illustrated waveform shown in FIG. 2(a), and comprises a succession of sensed atrial events 8 (P waves), such that the sensing of a P wave 8, releases immediately an atrial stimulation, corresponding to the pulse peak 9 (FIG. 2(a)). Consequently, both atria are simultaneously stimulated.

The atrial circuit 24 then senses the following ventricular depolarization wave 10 (an R wave) associated with the ventricle stimulation pulse peak 11 delivered to the right ventricle RV by the ventricular electrode 3. The temporal gap between the P wave and the following R wave corresponds to the atrium-ventricle conduction delay (schematized by the dashed arrow 12 on the FIG. 1). Of course, in case of a atrio-ventricular block or an anomaly of the same type, the ventricular circuit 23 of the pacemaker releases automatically the stimulation pulse if no ventricular R wave 10 is detected prior to the end of a predetermined AV delay interval.

In the particular case of the triple chamber stimulation, an atrial depolarization wave 8 can appear, in the absence of stimulation, in the manner illustrated in the larger scale of FIG. 2(b), namely in the form of a wave doublet 14, 15. In the wave doublet, wave 14 corresponds to the P wave $P_R$ of the right atrium RA and wave 15 corresponds to the P wave $P_L$ of the left atrium LA. The spacing between the two waves 14 and 15 depends on the inter-atrial delay (schematized as dashed arrow 16 in FIG. 1). The inter-atrial delay is variable according to each individual and, for each person, increases with the effort (activity level) of the patient.

As the inventors have realized, a ventricular wave depolarization, which has its origin at the level of the extremity terminal of electrode 3, can appear as an ectopic focus of excitation. In such case, the wave origin is not found at the location of the electrodes, i.e., approximately at the extremity of electrodes 3, 6. Rather, in some cases, it can be found at a point F in the left ventricle LV that is relatively close to the left atrium LA, for example, as illustrated in FIG. 1. Considering this relative proximity, the period of propagation from the focus F to the extremity terminal of the left atrial electrode 7, schematized as dashed arrow 17 in the FIG. 1, can be a short time duration. Indeed, the duration can be even shorter than the inter-atrial period schematized by dashed arrow 16.

Therefore, as the inventors have discovered, a depolarization waveform corresponding to an ectopic origin risks interfering with a depolarization wave front having an atrial origin, and being wrongly interpreted by the pacemaker as a subsequent atrial signal. As a result of the wrong interpretation, the pacemaker will release inopportunely an atrial stimulation. This is because the atrial stimulation is made synchronous with the atrial detection when the device is operating in a DDT mode. Such a premature atrial stimulation, which actually stimulates both of the atria, induces a tachycardia due to the existence of atrium-ventricle transmission 12 and, therefore, an anticipated contraction of the ventricle.

The result of this mechanism is a tachyarrhythmia that is identical in character to a tachycardia induced by the pacemaker (PMT). Hence, the inventors have discovered that this phenomenon of an electronically induced reentrant tachycardia (i.e., a PMT) which occurs in a significant number of patients with the use of the triple chamber pacemaker, is very probably the origin of the recurrent AT which have heretofore been known to exist with this type of device. Because the recurrent AT origin has been unexplained, it has been uncontrollable by operation of the device.

In order to minimize the recurrent AT phenomenon, the present invention proposes to operate a discrimination of signals sensed by the atrial circuit, and to operate the atrial stimulation only in response to a determined acceptable condition. This enhanced operation also functions to eliminate a response to the sensing of a sensed signal having an ectopic ventricular focus of excitation as an unacceptable condition.

Figure 2:
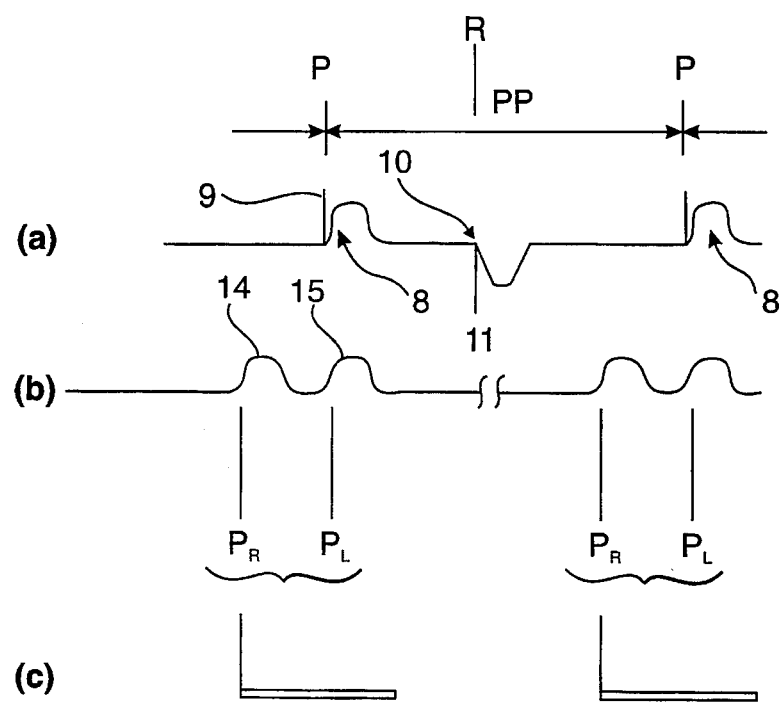
FIGS. 2(a) and 2(b) illustrate the succession over time of the various depolarization waves received by the atrial circuit of the pacemaker of FIG. 1.
FIG. 2(c) illustrates a masking refractory period, illustrating the signal discriminative principles of the present invention.

To operate the discrimination control, in accordance with a first embodiment of the invention, the atrial circuit senses and measures in a continuous manner (e.g., by a microprocessor of the pacemaker or by discrete sensing circuits with a counter) the interval between two successive sensed atrial signals, represented by interval PP in FIG. 2(*a*). This value is updated in response to each new signal sensed at the input of the atrial circuit.

Next, an evaluation is made, at each new acquired measure, of either the diminution or the rate of diminution of this interval of time, that is to say the difference (absolute or relative, respectively) with the preceding measured value. Then, the determined diminution or the rate of diminution is compared to a predetermined limit value, for example, a maximal diminution of 125 ms, or a maximal diminution rate of 25%. Other specific limit values can be used, for example, a diminution of between 50 and 350 ms, and a rate of diminution of between 12.5 and 37.5%.

If this limit value is not exceeded, it is considered that the situation is normal, i.e., an acceptable condition, and an atrial stimulation is immediately provided to both atria.

If the limit value is exceeded, one opens a "window of listening" on the ventricular electrode, for example, a duration of 31 or 50 ms. The listening window is used to detect the possible appearance of a signal at the input of the ventricular circuit 23. If a signal is sensed in the limit of this listening window, this means that the signal last sensed on the atrial electrode likely originated from an ectopic ventricular depolarization, corresponding to the propagation path schematized by dashed arrow 18 in FIG. 1. In this case, no atrial stimulation is provided, so as to avoid inducing the appearance of a PMT as explained earlier. If, however, no signal is received during the duration of this listening window, it is considered that the signal last sensed on the atrial electrode was effectively a signal originating from the atrium, and that the observed atrial event acceleration was in fact a physiological acceleration of the atrium. Accordingly, this is an acceptable condition and the atrium is then stimulated at the end of the listening window. The stimulation is delivered at the end of the listening window so as to preserve a minimal delay. In addition, the AV delay interval released on this last atrial detection will typically be lengthened to maintain at least a duration corresponding to the preceding cardiac cycle.

Another manner of the determination of the premature or non premature character of the P wave, according to a second embodiment of the invention, is to trigger on ventricular events. To this end, after each ventricular event (a detection or a stimulation) one releases a period of suspicion of a ventricular extrasystole corresponding to a fraction of the interval between two preceding P waves (a P—P interval), or between two preceding R waves (an R—R interval). The fraction may be defined as a relative value (e.g., x% of the preceding interval) or in an absolute value (e.g., the preceding interval less x milliseconds), for example, a diminution of between 50 and 350 ms, and a rate of diminution of between 12.5 and 37.5%. If one detects during this suspicion period a signal at the input of the atrial circuit 24, then there is a suspicion of the presence of a ventricular extrasystole, and, as described in the aforementioned implementation, a listening window is opened on the ventricular electrode. The control process then continues to examine signals using the listening window in the same manner and with the same possible results as previously described in connection with the first embodiment.

Advantageously, the improved control process based on the aforementioned signal discrimination techniques reduces the recurrent AT and counter-flow phenomenon, and avoids the need for medicinal supplement, thereby obtaining improved double atrial triple chamber pacing.

One skilled in the art will appreciate that the present invention can be practiced by other than the described embodiments, which are presented for purposes of illustration and not of limitation.

I claim:

1. A process for controlling a double atrial triple chamber cardiac pacemaker having an atrial circuit for detection and stimulation of the atrium, a ventricular circuit for detection and stimulation of the ventricle, a right atrial electrode, a left atrial electrode, the right and left atrial electrodes being connected to the atrial circuit, and a ventricular electrode connected to the ventricular circuit, comprising the steps of:

a) sensing at an input of the atrial circuit and the ventricular circuit a succession of depolarization signals;

b) sensing a depolarization signal at the input of the atrial circuit and determining whether or not the sensed depolarization signal has a prematurity character;

c) in case of a determined prematurity, examining during a predetermined listening window any depolarization signals sensed at the input of the ventricular circuit following said sensed depolarization signal, and:

i) in response to a sensed depolarization signal at the ventricular circuit input, inhibiting all atrial stimulation related to the determined prematurity, and ii) in the absence of a sensed depolarization signal at the ventricular circuit input, delivering an atrial stimulation at the end of the listening window; and d) in the absence of a determined prematurity, delivering an atrial stimulation synchronous to the sensed depolarization signal at the atrial circuit input.

2. The process of claim 1, in which step (b) comprises:

measuring the interval of time separating a first and a second successive sensed depolarization signals at the atrial circuit input;

determining one of the diminution and the rate of diminution of said measured interval of time based on a first measured interval and for a second measured interval following the first measured interval; and comparing the determined diminution or rate of diminution to a predetermined limit value and determining that the first sensed depolarization signal has said prematurity character in response to the predetermined limit value being exceeded.

3. The process of claim 1, in which step (b) comprises:

measuring an interval of time separating one of two successive depolarization signals sensed at the atrial circuit input and two successive depolarization signals sensed at the ventricular circuit input;

counting, beginning from the last sensed ventricular event, a period corresponding to a predetermined fraction of said measured interval of time;

analyzing during said period signals sensed at the input of the atrial circuit; and determining that the sensed depolarization signal has said prematurity character in response to an atrial signal being sensed during said period.

4. An apparatus for controlling a double atrial triple chamber cardiac pacemaker comprising:

an atrial circuit having an input to detect atrial events and to deliver stimulation pulses;

a first atrial electrode electrically connected to the atrial circuit input having a distal end to be coupled to one of the left and right atrium;

a second atrial electrode electrically connected to the atrial circuit input having a distal end to be coupled to the other of the left and right atrium;

a ventricular circuit having an input to detect ventricular events and to deliver stimulation pulses;

a ventricular electrode electrically connected to the ventricular circuit input and having a terminal to be coupled to a ventricle;

means for sensing a succession of depolarization signals at the inputs of the atrial and ventricular circuits;

means for determining whether or not a depolarization signal sensed at the input of the atrial circuit has a prematurity character;

means for processing the signal sensed at the input to the ventricular circuit during a predetermined time window in response to a sensed depolarization signal determined to have a prematurity condition;

means for controlling the delivery of an atrial stimulation operable in response to said processing means, wherein the occurrence of a ventricular signal sensed at the ventricular circuit input during the predetermined time window is operable to inhibit delivery of an atrial stimulation, and the absence of a ventricular signal sensed at the ventricular circuit input during said predetermined time window is operable to deliver a stimulation pulse at the end of the predetermined time window; and means for processing the depolarization signal sensed at the input to the ventricular circuit during a predetermined time window in response to said sensed depolarization signal at the atrial circuit input not having a prematurity condition to deliver an atrial stimulation synchronous to the sensed depolarization signal at the atrial circuit input.

5. The apparatus of claim 4, wherein the determining means further comprises:

a circuit to measure a time interval separating two successive atrial events;

means for determining a parameter corresponding to one of a diminution and a rate of diminution as between a first measured time interval and a second measured time interval following a first measured interval, and comparing the determined parameter to a predetermined limit value, wherein the prematurity character is present in response to the limit value being exceeded.

6. The apparatus of claim 4 wherein the determining means further comprises:

a circuit to measure a first time interval separating one of two successive atrial signals and two successive ventricular circuits;

means for timing a second time interval, beginning with the last sensed ventricular signal, corresponding to a predetermined fraction of said first time interval; and means for analyzing during said second time interval any signals sensed at the input of the atrial circuit, wherein the prematurity character is present in response to an atrial signal being sensed during said second time interval.

* * * * *